United States Patent
Mensah-Brown et al.

(10) Patent No.: US 9,970,993 B1
(45) Date of Patent: May 15, 2018

(54) SENSOR SYSTEM FOR MEASURING BATTERY INTERNAL STATE

(71) Applicant: Ford Global Technologies, LLC, Dearborn, MI (US)

(72) Inventors: Arnold Kweku Mensah-Brown, Canton, MI (US); Xinfan Lin, Davis, CA (US); Benjamin A. Tabatowski-Bush, South Lyon, MI (US); Richard Dyche Anderson, Plymouth, MI (US)

(73) Assignee: Ford Global Technologies, LLC, Dearborn, MI (US)

( * ) Notice: Subject to any disclaimer, the term of this patent is extended or adjusted under 35 U.S.C. 154(b) by 0 days. days.

(21) Appl. No.: 15/434,443

(22) Filed: Feb. 16, 2017

(51) Int. Cl.
| | |
|---|---|
| *H01M 4/00* | (2006.01) |
| *H01M 4/14* | (2006.01) |
| *H02P 27/00* | (2006.01) |
| *G01R 31/36* | (2006.01) |
| *B60L 11/18* | (2006.01) |
| *G01N 29/22* | (2006.01) |
| *G01N 29/24* | (2006.01) |
| *B60L 11/14* | (2006.01) |
| *B60R 16/02* | (2006.01) |
| *H01M 10/48* | (2006.01) |

(Continued)

(52) U.S. Cl.
CPC .......... *G01R 31/3679* (2013.01); *B60L 11/14* (2013.01); *B60L 11/1861* (2013.01); *B60L 11/1864* (2013.01); *B60R 16/02* (2013.01); *G01N 29/22* (2013.01); *G01N 29/2412* (2013.01); *H01M 2/1077* (2013.01); *H01M 10/482* (2013.01); *B60L 2210/10* (2013.01); *B60L 2240/42* (2013.01); *B60L 2240/545* (2013.01); *B60Y 2400/112* (2013.01); *G01N 2291/0423* (2013.01); *H01M 2010/4271* (2013.01); *H01M 2220/20* (2013.01); *Y10S 903/907* (2013.01)

(58) Field of Classification Search
USPC .......... 318/139; 429/10, 400, 498, 527, 535
See application file for complete search history.

(56) References Cited

U.S. PATENT DOCUMENTS

| | | | |
|---|---|---|---|
| 4,865,931 A | 9/1989 | McCullough, Jr. et al. | |
| 5,786,040 A * | 7/1998 | Leddy | B03C 1/01 204/290.11 |

(Continued)

OTHER PUBLICATIONS

Buchmann, I., "Battery Fuel Gauge: Factual or Fallacy?", 9-1-1 Magazine, Jan. 20, 2012, 4 pgs.

*Primary Examiner* — Bentsu Ro
(74) *Attorney, Agent, or Firm* — David B. Kelley; Brooks Kushman P.C.

(57) ABSTRACT

Systems and methods for sensing internal states of vehicle batteries are described. From this internal state information, various physical characteristics of the battery can be measured, calculated or inferred. A vehicle can include an electric motor, a battery to store electrical energy for the electric motor, and a sensor connected to the battery to sense a battery state, to receive an input signal, and to wirelessly transmit an output signal indicating the battery state. The sensor may be passive and built into the structure of the battery. The sensor can be a surface wave acoustic sensor with a magnetic field sensor, which can be a magnetoimpedance sensing device and a temperature sensor.

20 Claims, 8 Drawing Sheets

(51) Int. Cl.
    *H01M 2/10*         (2006.01)
    *H01M 10/42*      (2006.01)

(56) References Cited

U.S. PATENT DOCUMENTS

| | | | |
|---|---|---|---|
| 5,928,804 A * | 7/1999 | Leddy | B03C 1/01 |
| | | | 429/10 |
| 6,184,656 B1 | 2/2001 | Karunasiri et al. | |
| 6,479,176 B2 * | 11/2002 | Leddy | B03C 1/01 |
| | | | 428/692.1 |
| 7,417,405 B2 | 8/2008 | Carrier et al. | |
| 7,425,816 B2 | 9/2008 | Meyer et al. | |
| 7,936,151 B2 | 5/2011 | Bucur et al. | |
| 7,944,181 B2 | 5/2011 | Johnson et al. | |
| 8,278,876 B2 | 10/2012 | Bucur et al. | |
| 8,384,524 B2 * | 2/2013 | Cobianu | G06K 19/0672 |
| | | | 235/375 |
| 8,817,428 B2 * | 8/2014 | Perez | H01G 2/14 |
| | | | 361/15 |
| 8,994,370 B2 | 3/2015 | Pannetier-Lecoeur et al. | |
| 2009/0115420 A1 | 5/2009 | Koch et al. | |
| 2010/0227222 A1 * | 9/2010 | Chang | C01D 15/00 |
| | | | 429/231.95 |
| 2012/0086457 A1 | 4/2012 | Meisner et al. | |
| 2012/0089299 A1 | 4/2012 | Breed | |
| 2012/0161776 A1 | 6/2012 | Koch et al. | |
| 2013/0057288 A1 | 3/2013 | Ogata et al. | |
| 2013/0149565 A1 | 6/2013 | Conell et al. | |
| 2013/0187645 A1 | 7/2013 | Pannetier-Lecoeur et al. | |
| 2014/0297084 A1 | 10/2014 | Meisner et al. | |

\* cited by examiner

SENSOR SYSTEM FOR MEASURING BATTERY INTERNAL STATE

TECHNICAL FIELD

Various embodiments relate to systems and methods for sensing a battery state, and a vehicle using such systems and methods.

BACKGROUND

Batteries used in vehicles may be monitored using various sensors to determine physical properties of the battery. Temperature of a battery can be approximated by a measurement of a thermistor on the bus bar attached to a battery; temperature sensors may also be mounted directly on the cell case. Battery cell voltage can be measured using a chip that may be multiplexed to a plurality of battery cells, connected with physical wiring through a battery housing, and drawing electrical power from the battery cell itself. Present art for current measurement uses either a resistive shunt or a Hall Effect current sensor that generates a difference in electric potential across the sides of a current-carrying conductor that is connected to the battery. As there is a desire to increase efficiency of vehicles powered by batteries, more accurate data regarding battery physical state may result in improved performance.

SUMMARY

Systems and methods for sensing the internal states of batteries for vehicles are described. From this internal state information, various physical characteristics of the batteries can be measured, calculated or inferred.

An electric vehicle, e.g., a hybrid electric vehicle (HEV), can include an electric motor, a battery to store electrical energy for the electric motor, and a sensor connected to the battery to sense a battery state, to receive an input signal, and to wirelessly transmit an output signal indicating the battery state, and control circuitry to receive the output signal and to control the electric motor and the battery. In certain examples, the battery may have a physical property that changes based on a state of the battery. This physical property may be measured by the sensor. The sensor may be passive and built into the structure of the battery.

In an example, an electric or hybrid vehicle may comprise an electric motor; a battery to store electrical energy for the electric motor; and surface acoustic wave sensor to wirelessly sense a magnetic field of the battery and temperature of the battery, the sensor including a magnetic field reactive device to change a surface wave in response to the magnetic field.

In an example, the sensor includes a passive radio frequency identification tag.

In an example, control circuitry configured to control the electric motor and the battery based on an output signal from the surface acoustic wave sensor.

In an example, the control circuitry determines a battery state from the output signal from the surface acoustic wave sensor.

In an example, the battery state is state of charge (SOC) or state of health (SOH).

In an example, the sensor is embedded in a housing of the battery and wirelessly communicates with control circuitry of the motor.

In an example, the sensor includes a plurality of acoustic reflectors, and is further configured to convert an input signal to a surface wave acoustic signal that is reflected by the reflectors to produce the response signal and modified by the magnetic field reactive device.

In an example, the magnetic field reactive device includes a giant magnetoimpedance (GMI) thin film.

In an example, a mechanical absorber on the surface acoustic wave (SAW) substrate adjacent the GMI thin film and matching circuitry electrically connecting the GMI thin film to the acoustic reflector.

In an example, the acoustic reflector includes an interdigated reflector with a finger having at thickness of $\lambda/8$ relative to a signal on the SAW substrate. It is noted that $\lambda$ is the wavelength of the propagating wave.

In an example, the surface acoustic wave sensor includes circuitry to convert sensed magnetic field to an output voltage.

The present description further includes a battery monitoring system, which may include a surface acoustic wave sensor to wirelessly sense a state of the battery and having a magnetic field sensing device to modify a SAW signal based on a magnetic field at a battery electrode, a temperature sensor to sense temperature at a battery, and a transducer to wirelessly output a signal including temperature and battery state; and control circuitry to convert the sensed magnetic field to an output voltage signal.

In an example, the sensor includes a passive radio frequency identification tag.

In an example, the output voltage represents the strength of the magnetic field, which directly relates to the degree of lithiation in the battery. A state of charge (SOC) or state of health (SOH) of the battery can be correlated or determined from the output voltage signal.

In an example, the sensor is embedded in a housing of the battery.

In an example, the sensor includes a plurality of acoustic reflectors, and the magnetic field sensing device includes a GMI thin film connected to at least one of the acoustic reflectors.

In an example, the magnetic field sensing device includes a mechanical absorber adjacent to one of the acoustic reflector and the GMI thin film.

In an example, the magnetic field sensing device includes matching circuit connected to the reflector and the GMI thin film.

In an example, the transducer includes conversion circuitry to convert the sensed magnetic field to an output signal to be wirelessly transmitted from the surface acoustic wave sensor to external circuitry at a vehicle.

In an example, the acoustic reflector includes an interdigitated reflector with a finger having at thickness of $\lambda/8$ relative to a signal on the SAW substrate.

In an example, the SAW sensor is calibrated to set the two extreme deflections of the sensor to represent 0% lithiation and 100% lithiation at the battery terminal as the two extreme positions of the sensor. These two extreme positions of the sensor allow the sensor to be in its range of sensing such that it can more accurately sense degree of lithiation, which can be used to derive the battery capacity and battery state of charge.

The present disclosure also describes a rechargeable battery monitoring system that may comprise any of the above examples. Such a monitoring system can be used with a vehicle, such as an automobile, a hybrid electric vehicle, a mobile electronic device, a mobile communication device, and the like.

A battery state determination method is also disclosed and may include wirelessly transmitting an input signal, receiving the input signal by a passive sensor connected to a battery, outputting an output signal that changes based on a modulus of the battery, and determining battery state using the output signal.

DETAILED DESCRIPTION

The present document details embodiments of the present invention herein; however, it is to be understood that the disclosed embodiments are merely exemplary of the invention that may be embodied in various and alternative forms. The figures are not necessarily to scale; some features may be exaggerated or minimized to show details of particular components. Therefore, specific structural and functional details disclosed herein are not to be interpreted as limiting, but merely as a representative basis for teaching one skilled in the art to variously employ the present invention. As those of ordinary skill in the art will understand, various features illustrated and described with reference to any one of the figures can be combined with features illustrated in one or more other figures to produce embodiments that are not explicitly illustrated or described. The combinations of features illustrated provide representative embodiments for typical applications. Various combinations and modifications of the features consistent with the teachings of this disclosure, however, could be desired for particular applications or implementations.

Figure 1:
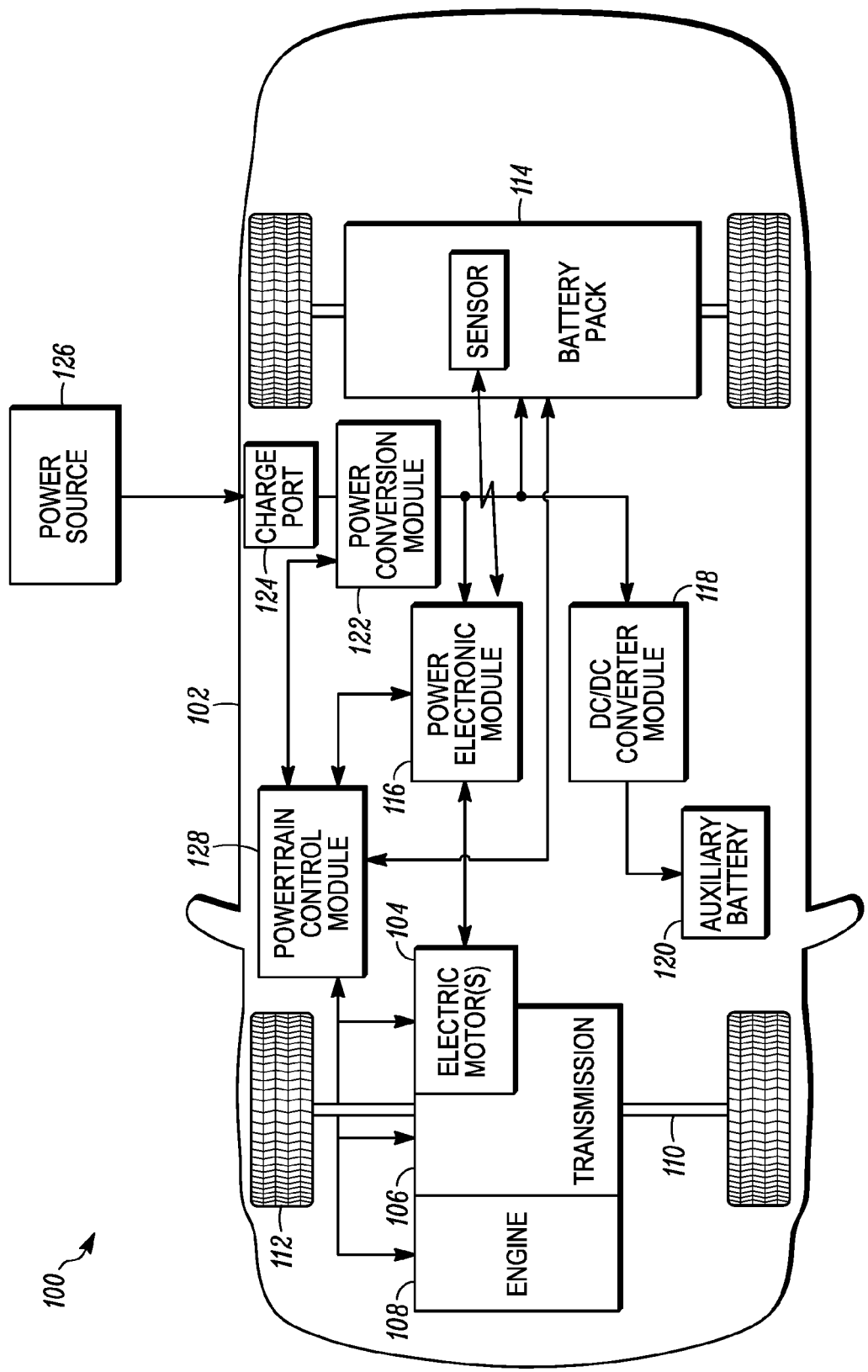
FIG. 1 is an example electric vehicle with a battery pack.

FIG. 1 depicts an example of an electric vehicle system 100. The system 100 can include an electric vehicle 100 can be a hybrid electric vehicle, a fully electric vehicle or the like with a traction battery. The system 100 can further include a power source 126 to charge the electrical vehicle 102. The electric vehicle 102 may comprise one or more electric motors 104 mechanically connected to a hybrid transmission 106. In addition, the hybrid transmission 106 is mechanically connected to an engine 108, for example an internal combustion engine. The hybrid transmission 106 may also be mechanically connected to a drive shaft 110 that is mechanically connected to the wheels 112. The electric motors 104 can provide propulsion when the engine 108 is turned on. The electric motors 104 can provide deceleration capability when the engine 108 is turned off. The electric motors 104 may be configured as generators and can provide fuel economy benefits by recovering energy that would normally be lost as heat in the friction braking system. The electric motors 104 may also reduce pollutant emissions since the electric vehicle 102 may be operated in electric mode under certain conditions.

The traction battery or battery pack 114 stores energy that can be used by the electric motors 104. A vehicle battery pack 114 typically provides a high voltage DC output, e.g., greater than 100 volts, greater than 200 volts, greater than 300 volts, in various examples. The battery pack 114 is electrically connected to a power electronics module 116. The power electronics module 116 is also electrically connected to the electric motors 104 and provides the ability to bi-directionally transfer energy between the battery pack 114 and the electric motors 104. For example, a battery pack 114 may provide a DC voltage while the electric motors 104 may require a three-phase AC current to function. The power electronics module 116 may convert the DC voltage to a three-phase AC current as required by the electric motors 104, for example, by using an inverter module. In a regenerative mode, the power electronics module 116 will convert the three-phase AC current from the electric motors 104 acting as generators to the DC voltage required by the battery pack 114, also using an inverter module or other circuitry. The methods described herein are equally applicable to a pure electric vehicle or any other device or vehicle using a battery pack.

In addition to providing energy for propulsion, the battery pack 114 may provide energy for other vehicle electrical systems. Such a system may include a DC/DC converter module 118 that converts the high voltage DC output of the battery pack 114 to a low voltage DC supply that is compatible with other vehicle loads. Other high voltage loads, such as compressors and electric heaters, may be connected directly to the high-voltage bus from the battery pack 114. In a vehicle, the low voltage systems may be electrically connected to a 12V battery 120. An all-electric vehicle may have a similar architecture but without the engine 108.

The battery pack 114 may be recharged by the external power source 126. The external power source 126 may provide AC or DC power to the vehicle 102 by electrically connecting through a charge port 124. The charge port 124 may be any type of port configured to transfer power from the external power source 126 to the vehicle 102. The charge port 124 may be electrically connected to a power conversion module 122. The power conversion module may condition the power from the external power source 126 to provide the proper voltage and current levels to the battery pack 114. In some applications, the external power source 126 may be configured to provide the proper voltage and current levels to the battery pack 114 and the power conversion module 122 may not be necessary. The functions of the power conversion module 122 may reside in the external power source 126 in some applications. The vehicle engine, transmission, electric motors, battery, power conversion and power electronics may be controlled by a powertrain control module (PCM) 128.

The battery pack 114 can include a plurality of cells that have electrodes to electrically connect the cell to other circuitry. The battery parameters and status can be sensed by placing passive sensors in the battery pack or in each battery cell. A signal external to the battery can interrogate the sensor. In an example, the signal also energizes the sensor. The sensor can include radio frequency identification tag devices as well as battery sensing circuitry and other technological devices. The sensor then sends a sensed signal outside the battery pack to a receiver that is connected to other vehicle circuitry.

In addition to illustrating a plug-in hybrid vehicle, FIG. 1 can illustrate a battery electric vehicle (BEV) if engine 108 is removed. Likewise, FIG. 1 can illustrate a traditional hybrid electric vehicle (HEV) or a power-split hybrid electric vehicle if components 122, 124, and 126 are removed. FIG. 1 also illustrates the high voltage system which includes the electric motor(s), the power electronics module 116, the DC/DC converter module 118, the power conversion module 122, and the battery pack 114. The high voltage system and battery pack includes high voltage components including bus bars, high voltage connectors, high voltage wires, and circuit interrupt devices.

Figure 2:
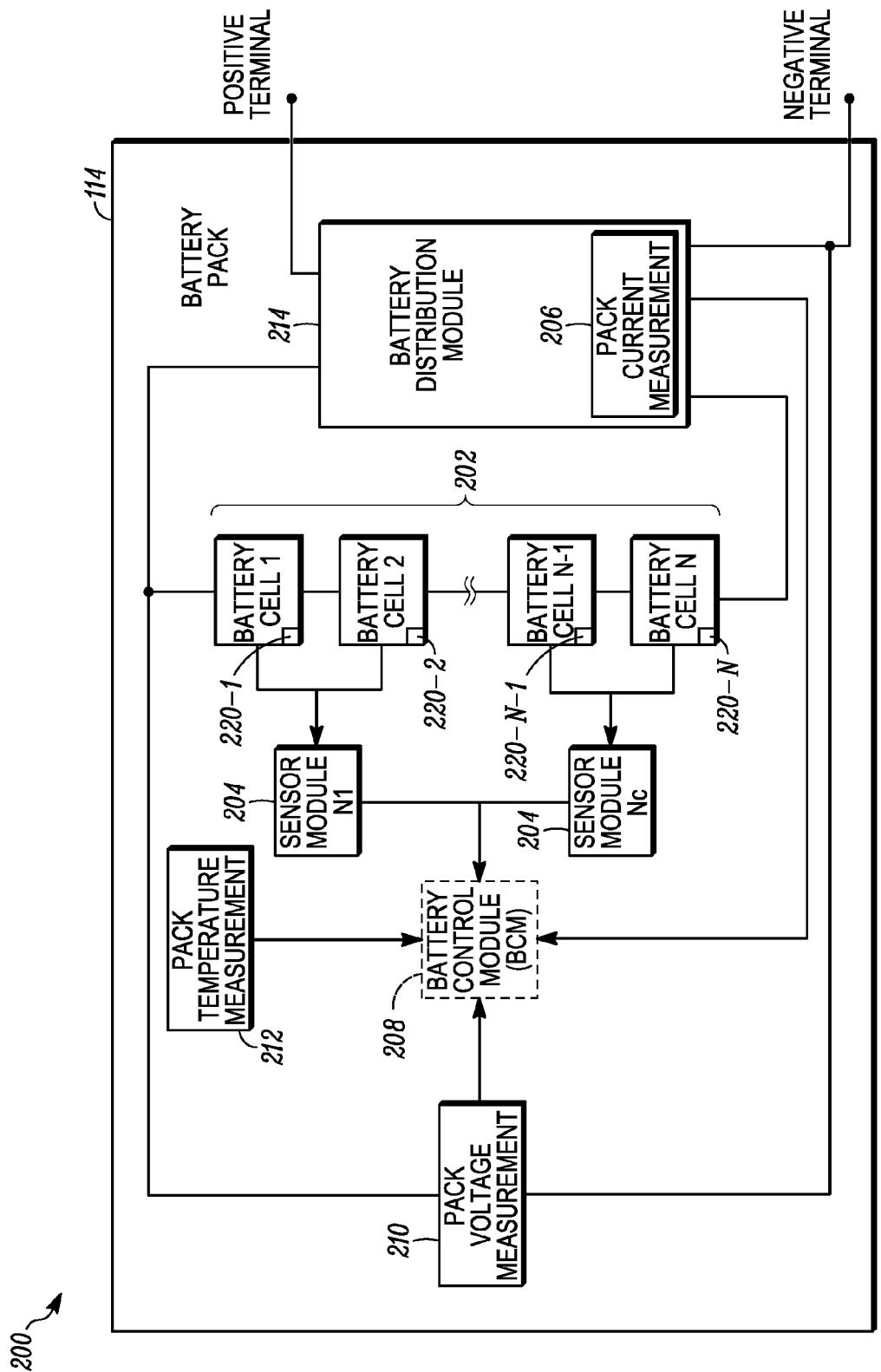
FIG. 2 is a battery pack arrangement comprised of battery cells and battery cell monitoring and controlling systems.

The individual battery cells within a battery pack can be constructed from a variety of chemical formulations. Battery pack chemistries may include, but are not limited, to Lithium-Ion, Lithium-Ion polymer lead acid, nickel cadmium (NiCd), or nickel-metal hydride (NIMH. FIG. 2 shows a battery pack 200 in a simple series configuration of N battery cell modules 202. The battery cell modules 202 may contain a single battery cell or multiple battery cells electrically connected in parallel with the connections being made at electrodes. The battery pack, however, may be composed of any number of individual battery cells and battery cell modules connected in series or parallel or some combination thereof. A system may have one or more controllers, such as a Battery Control Module (BCM) 208 that monitors and controls the performance of the battery pack 200. The BCM 208 may monitor several battery pack level characteristics such as pack current measured by a current sensor 206, pack voltage 210 and pack temperature 212. The performance of the current sensor 206 may be used, in certain arrangements, to build a reliable battery monitoring system. The accuracy of the current sensor may be useful to estimate the battery state of charge and capacity. A current sensor may utilize a variety of methods based on physical principles to detect the current including a Hall Effect IC sensor, a transformer or current clamp, a resistor in which the voltage is directly proportional to the current through it, fiber optics using an interferometer to measure the phase change in the light produced by a magnetic field, or a Rogowski coil. In the event a battery cell is charging or discharging such that the current entering or exiting the battery cell exceeds a threshold, the battery control module may disconnect the battery cell via the use of a circuit interrupt device (CID) such as a fuse or circuit breaker.

The battery cell may exhibit physical changes, such as swelling and contraction (which changes the cell's Young's modulus), as state of charge changes. In the case of a lithium (Li) ion battery including an electrode made of metal oxides and Li ions, Li is inserted into and de-inserted from the electrode during discharging and charging, respectively. This process induces micro-structural changes (swelling and contraction), thus changing the modulus (a material property) of the electrode. For example, the modulus of graphite increases with lithium insertion. Young's Modulus for a graphite electrode changes by nearly a factor of 3 when full of Li. The change in modulus can be measured according to the systems and methods described herein, e.g., a sensor at or within the battery cell or battery pack.

In addition to the pack level characteristics, there may be battery cell level characteristics that need to be measured and monitored. For example, the terminal voltage, current, and temperature of each cell or a representative subset of cells may be measured. A system may use a sensor module 204 to measure the characteristics of one or more battery cell modules 202. The characteristics may include battery cell voltage, temperature, age, number of charge/discharge cycles, etc. In an example, a sensor module 204 will measure battery cell voltage. Battery cell voltage may be voltage of a single battery or of a group of batteries electrically connected in parallel or in series. The battery pack 114 may utilize up to $N_c$ sensor modules 204 to measure the characteristics of a representative sample or all of the battery cells 202. The sensor modules 204 may communicate battery cell sensors 220. Battery cell sensors 220-1, 220-2, . . . 220-N-1 and 220-N are fixed to each battery cell 1, 2, N-1, N. The battery cell sensors can be passive sensors, e.g., radio frequency identification tags, surface acoustic wave sensors, or other similar sensors, that are integral with the battery cell structure. The battery cell sensors 220 can sense a physical property of the battery cell and produce an output signal that can be received by the sensor module 204 in response to the measured battery cell physical property. Each sensor module 204 may transfer the measurements to the BCM 208 for further processing and coordination. The sensor module 204 may transfer signals in analog or digital form to the BCM 208. The battery pack 114 may also contain a battery distribution module (BDM) 214 which controls the flow of current into and out of the battery pack 114.

Figure 3A:
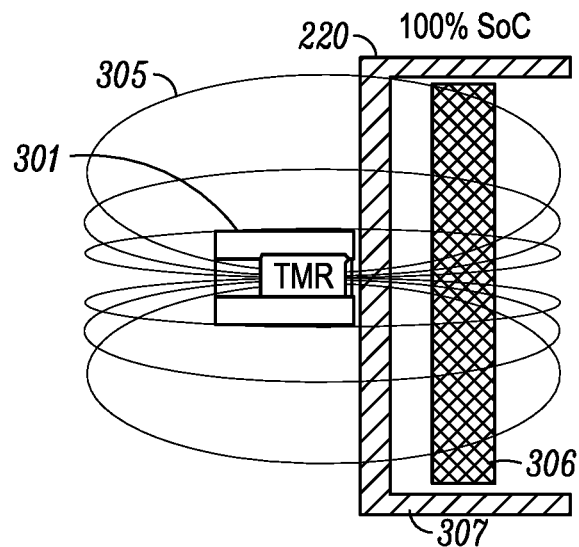
FIGS. 3A and 3B show a sensor according to the teachings herein that has a different sensor reading based on a physical characteristic of a battery cell.
Figure 3B:
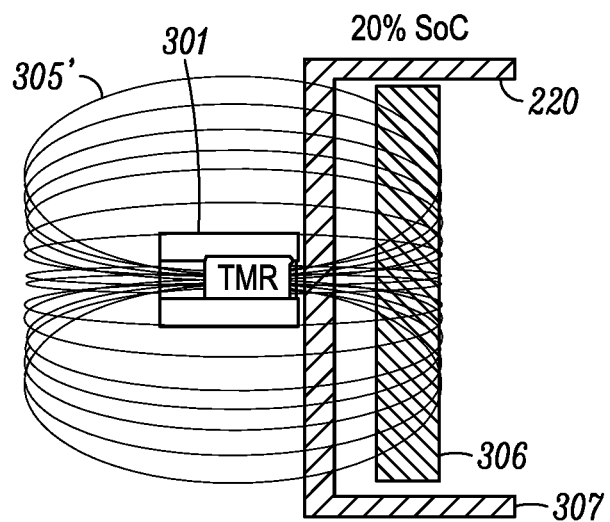

FIGS. 3A and 3B show sensor 301 according to the teachings herein for reading a physical characteristic of a battery cell. Sensor 301 is adjacent the battery cell 220. Sensor 301 can sense a signal 305 (305' in FIG. 3B) to determine the characteristic of the battery. The sensor 301 can be a tunneling magnetoresistance (TMR) device with two magnetic layers (e.g., ferromagnets such as CoFeB) separated by a thin insulator (e.g., MgO that is a few atoms thick) that can emit and sense a magnetic field. A TMR device uses a quantum mechanical process to read the magnetic field through a process called tunneling. A biasing voltage is created between the metals, by allowing current to flow across the insulator. The likelihood of quantum tunneling is directly related to electron spin alignment, which can be manipulated and controlled by introducing external magnetic fields, with the following consequence: as the strength of the magnetic field increases, the electron spin alignment increases, and more electrons may tunnel across the insulator. As more electrons tunnel across the insulator, the resistance of the device falls. Accordingly, the magneto resistance of the sensor is the first indication of its performance: for example, anisotropic sensors have 2-3% magneto resistance, whereas giant sensors have 15-20% magneto resistance. By contrast, sensors that implement magnetic tunnel junctions have a magneto resistance of 200%.

In an example, the sensor 301 is positioned adjacent an electrode 306 of the battery within a battery housing 307. A physical characteristic of the electrode 306 at a first state results in a first signal field 305. A change in the physical characteristic of the electrode 306 at a second state results in a second signal field 305'. In an example, the electrode 305 includes battery anode materials for lithium (Li) ion batteries and includes metal oxides and Li ions which can readily be inserted and withdrawn from the oxides. Li is a paramagnetic material and hence anode magnetic properties (i.e., magnetic susceptibility) changes during charge and discharge cycles. In the presence of a magnetic field 305, the anode becomes magnetized. The magnetic field 305 for a fully charged battery can be sensed and used as a baseline (FIG. 3A). As the battery discharges, the magnetic field will be perturbed 305' and will directly measure the state of charge (SOC) of the battery as shown in FIG. 3B. FIG. 3A shows a magnetic field 305 response of a battery that is 100% SOC. FIG. 3B shows a magnetic field 305' response of a battery that is 20% SOC. A battery with a lower charge has a measurable increase in magnetic susceptibility and hence there is a greater magnetic field compared to batteries with greater charge states. In the present example, the battery electrode for a battery with 20% state of charge has a three-fold increase in magnetic susceptibility compared to one that is fully charged.

The positive electrode, i.e., a metal oxide, and lithium ion ($Li^+$) of Li-ion batteries are paramagnetic materials because of their electronic structure. The Li ions can readily be withdrawn from and inserted into the oxides during charge and discharge cycles, respectively. This leads to the changing magnetic properties (i.e., magnetic susceptibility) of the positive electrode. In the presence of a magnetic field, the positive electrode becomes magnetized. The magnetic field for a fully charged battery can be sensed and used as a baseline for analysis as described herein. As the battery charges/discharges, the magnetic field will be perturbed by the withdrawal/insertion of $Li^+$ and this will directly measure the degree of lithiation. The degree of lithiation is related to SOC and degradation of battery. Lithiation may represent the degree or amount of lithium that is incorporated onto a battery electrode.

FIGS. 3A and 3B shows the magnetic field response of a fully charged battery (100% SOC) to one that is discharged (e.g., 20% SOC). In the present example, a positive electrode for a battery with 20% SOC has about three times increase in magnetic susceptibility compared to one that is fully charged. While the above example describes lithium ion batteries, this sensing principle may be used for sensing other battery types that use paramagnetic electrode materials, e.g., lead acid batteries.

Furthermore, the proposed technology can also be used to determine battery capacity over lifetime with better accuracy. It is well known that battery performance will degrade over time due to capacity fade and impedance growth. A main cause for capacity fade is loss of active lithium. It is critical for the battery management system (BMS) to track the capacity change in real time for batteries which are used across a wide range of SOC, such as a PHEV or BEV. The proposed technology avoids the errors mentioned in the problem statement above by directly measuring the lithium content at the minimum and maximum battery voltage thresholds.

While the above example describes lithium ion batteries, this technique may be used for sensing other battery types, e.g., lead acid batteries and lithium iron phosphate batteries.

The sensor 301 can be a passive sensor that does not need to emit a signal and it senses the magnetic field of the battery electrode. The change in the sensed magnetic field can indicate change in a physical characteristic of the battery.

In use, the SAW sensor 301 is calibrated to set the two extreme deflections of the sensor to represent 0% lithiation and 100% lithiation at the battery terminal as the two extreme positions of the sensor. These two extreme positions of the sensor allow the sensor to be in its range of sensing such that it can more accurately sense degree of lithiation, which can be used to derive the battery capacity and battery state of charge.

Figure 4:
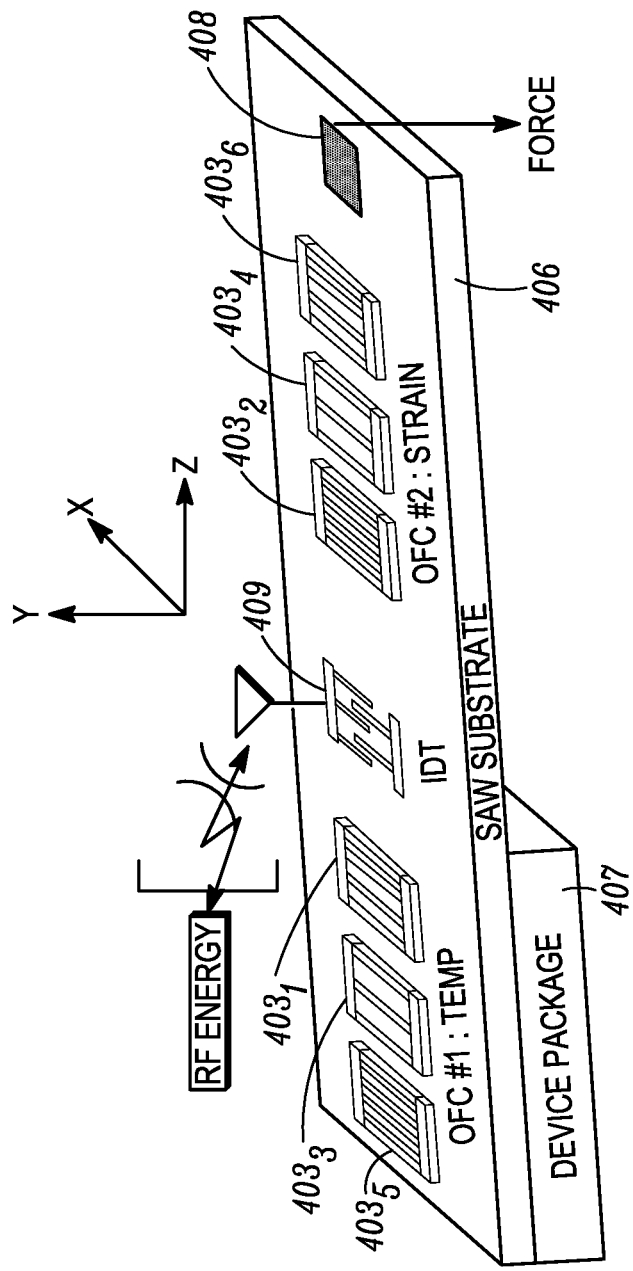
FIG. 4 is a view of a sensor for use with a battery cell, according to an example embodiment.

FIG. 4 shows a schematic view of a sensor 400 for a battery or battery cell. The sensor can be a surface wave acoustic sensor. The sensor 400 can include a one-port dual delay, orthogonal frequency coding (OFC) with multiple reflectors on the substrate 406. Other wireless coding can be used to send information and energy signals to the sensor 400. The reflectors can be integrated circuits, microelectromechanical systems, or the like. A device package 407 supports the substrate 406 at one end portion such that the other end is cantilevered and can deflect. The deflection movement can be sensed and the resulting data can represent the battery states or other battery information. The substrate 406 can be a YZ $LiNbO_3$ structure in an example. In FIG. 4, there is shown three reflectors per OFC bank ($403_1$-$403_6$) for a total of six reflectors in two banks on opposite sides of the transducer 409. The chips $403_1$-$403_6$ can be surface acoustic wave acoustic devices that receive a surface wave from the transducer 409 and return a signal to the transducer 409 indicating information relating to the battery. The battery can place a strain on the saw substrate 406 that is sensed by the signal to/from the reflectors $403_1$-$403_6$. The bank of reflectors $403_1$, $403_3$, and $403_5$ are positioned at the end portion of the substrate that is directly supported by the package 407. Reflectors $403_1$, $403_3$, and $403_5$ can measure the temperature at the battery, either in the battery adjacent the internal battery chemistry or on the battery package or case. Reflectors $403_1$, $403_3$, and $403_5$ can also provide a non-strained or displaced baseline signal, which can be used when determining strain or displacement at the other end of the sensor 400. The second bank of reflectors $403_2$, $403_4$, and $403_6$ are positioned at the end portion of the substrate that is not directly supported by the package 407. The second bank of reflectors $403_2$, $403_4$, and $403_6$ are an end of the substrate 406 that is the free end of the cantilevered substrate. Reflectors $403_2$, $403_4$, and $403_6$ can measure the strain experienced by the substrate, either in the battery adjacent the internal battery chemistry or on the battery package or case. In an example, the strain can be caused by a magnet 408 positioned at the free end of the cantilevered substrate. The magnet 408 produces a magnetic field and senses changes in the battery via the electromagnetic fields in the battery. In an example, the magnet 408 senses the magnetic field in the adjacent region of the vehicle battery. As the magnet 408 electromagnetically interacts with the magnetic field of the battery, the substrate is moved and its displacement can be sensed by the reflectors $403_2$, $403_4$, and $403_6$. While described herein as reflectors, the reflectors $403_1$-$403_6$ can include electronic structures, MEMS structures or combinations thereof. The sensor 400 can include the interdigitated transducers as described herein.

Figure 5:
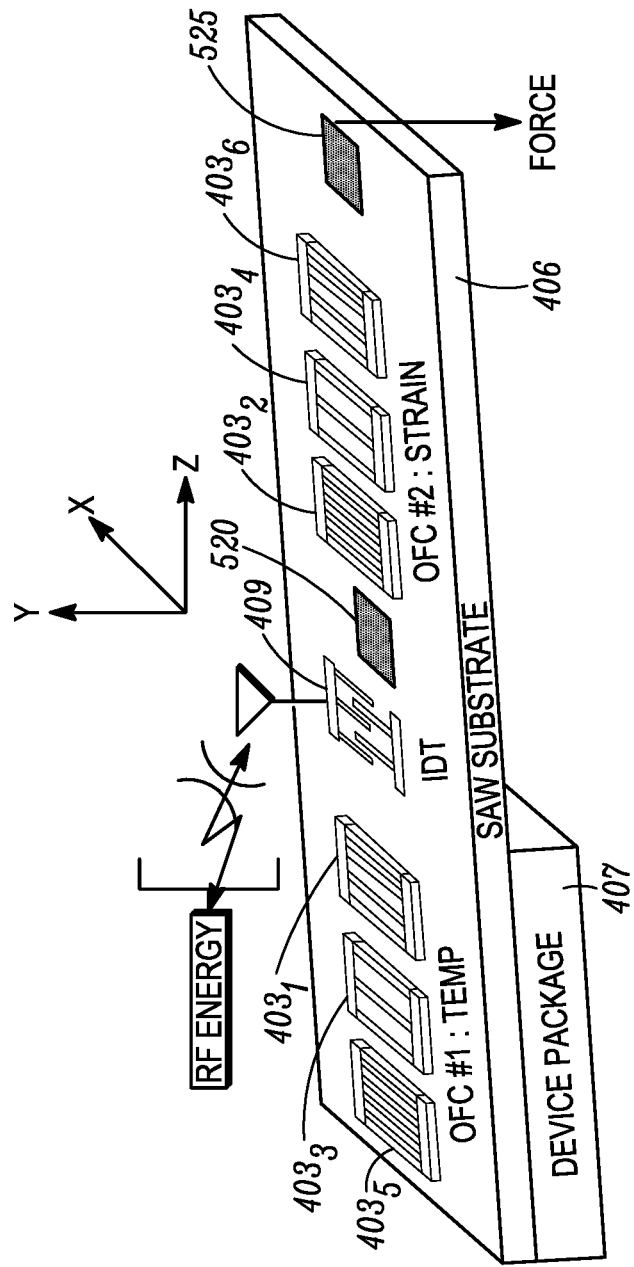
FIG. 5 is a view of a sensor for use with a battery cell, according to an example embodiment.
Figure 6:
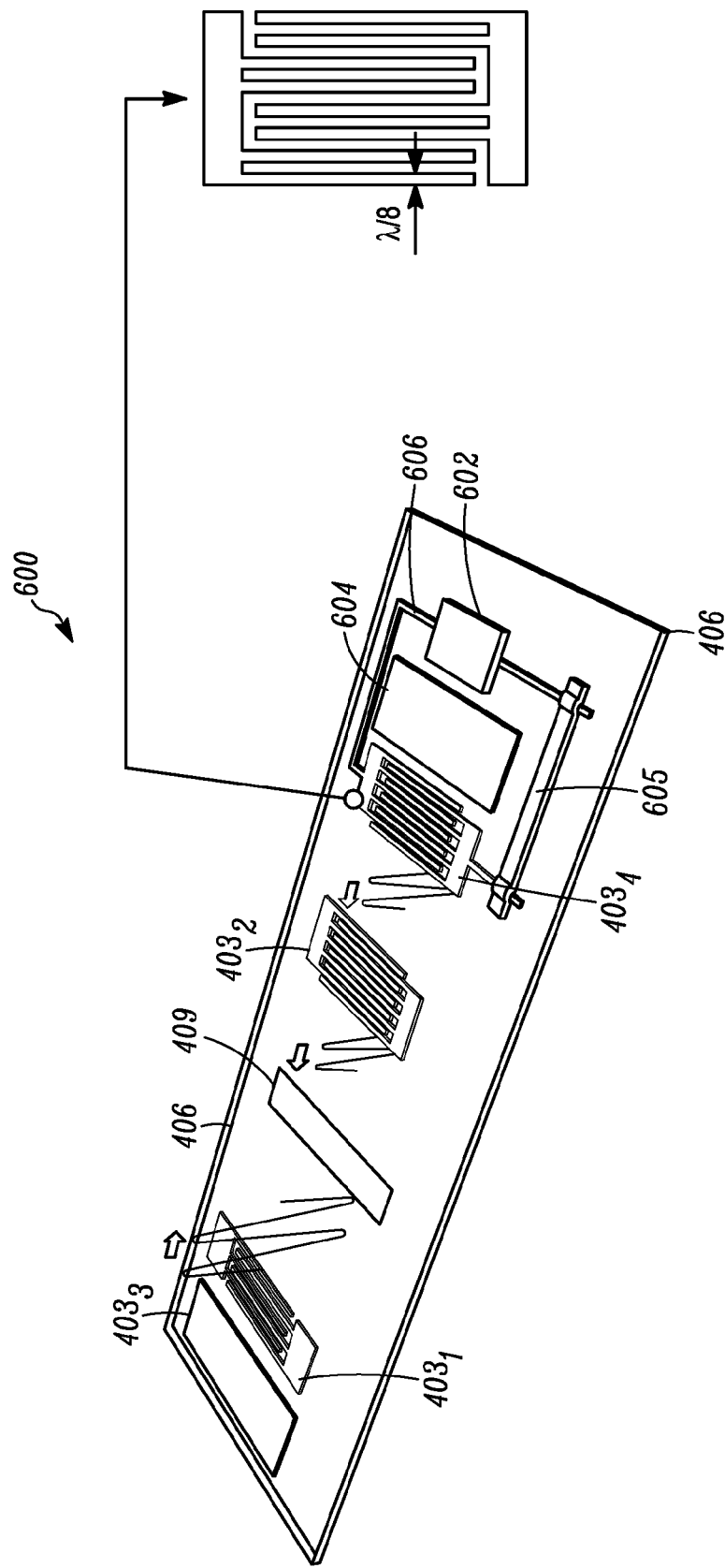
FIG. 6 is a view of a sensor for use with a battery cell, according to an example embodiment.

Surface acoustic wave (SAW) based devices, which can be designed for either wired or wireless operation, provide a sensor platform for measuring active lithium concentration via magnetic field sensing. These sensors are based on the piezoelectric effect whereby the signal propagation velocity of a SAW in a piezoelectric substrate changes in response to surface perturbation. SAW devices are sensitive to temperature, pressure, stress, liquid viscosity, and surface effects. In order to measure the magnetic field response for a charged/discharged cell, the surface of the SAW will have to be modified with a magnetic element to convert the magnetic field change into a surface perturbation. In various examples, the propagation path in the saw substrate can be overlaid with a magnetoresistive (MR) film, giant magnetoimpedance (GMI) thin film or embedding a permanent magnet in a cantilever structure of the saw substrate, as illustrated in FIGS. 4 to 6, respectively. Among the available magnetic field sensors, SAW-based thin film GMI offers favorable characteristics like high frequency sensitivity to magnetic field, compatibility with high frequency operation and standard microfabrication procedures, and easy integration with SAW devices and electronic circuits.

FIG. 5 shows a schematic view of a sensor 500 for a battery or battery cell, which is similar to the sensor 400 described above with regard to FIG. 4. The sensor 500 includes a film device 520 that can be a magnetoresistive (MR) film or a giant magnetoimpedance (GMI) thin film, which can change the perturbation of the signal on the SAW substrate in response to the magnetic field of an electrode of a battery cell. The sensor 500 includes a second film device 525 that can be a magnetoresistive (MR) film or a giant magnetoimpedance (GMI) thin film, which can change the perturbation of the signal on the SAW substrate in response to the magnetic field of an electrode of a battery cell. The SAW sensor 500 can have one or both of the device s 520 and 525. The first device 520 can be placed toward the center of the saw substrate 406, e.g., adjacent the input/output transducer 409 or between the transducer 409 and the strain sensing devices $403_2$, $403_4$ and $403_6$. The second device 525 may be positioned otherwise on the saw substrate 406.

FIG. 6 shows a schematic view of a sensor 600 for a battery or battery cell. The sensor 600 can be a surface wave acoustic sensor, which is similar to the sensors 400, 500 described above.

Figure 7:
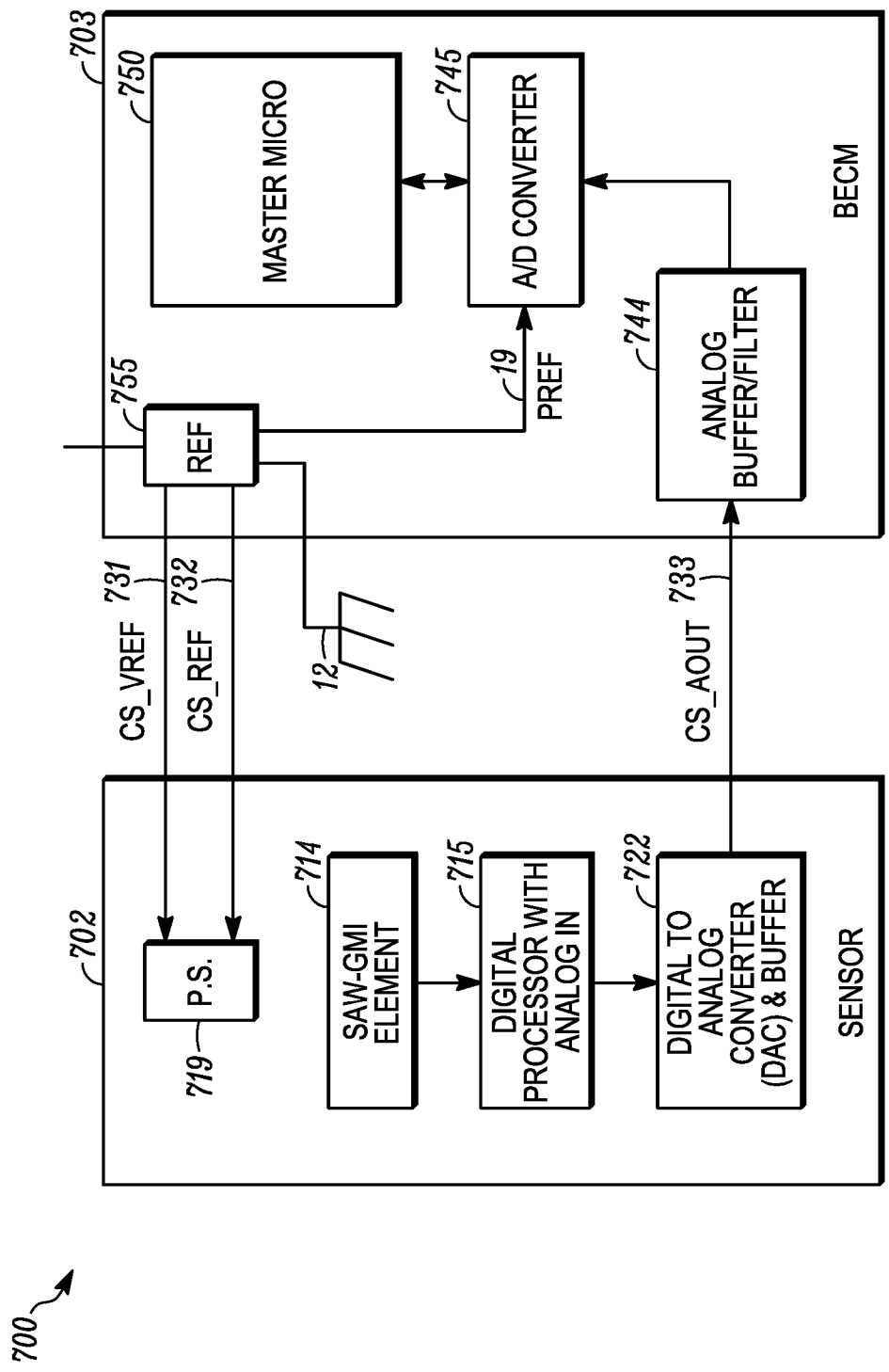
FIG. 7 is a schematic view of a battery sensor system for an electric vehicle, according to an example embodiment.

FIG. 7 shows a partial vehicle system 700 with a SAW sensor subsystem 702 with a magnetic field sensor and with an electronic control module 703. In various embodiments described herein the magnetic sensor element consists of a GMI thin film sensor integrated with into SAW system. In an example embodiment, the magnetic sensor element may just be a GMI sensor. As mentioned earlier, the integrated SAW-GMI sensor may be wireless.

In order to obtain high sensitivity to magnetic field, the GMI sensor 714 is matched to the output port, e.g., transducer 409 (FIG. 6) at the working frequency of the SAW system, e.g., 400, 500, or 600. As the impedance of the GMI sensor 714 changes with the applied magnetic field from the battery, the matching deteriorates, which causes the amplitude of the signal reflected from reflector $403_2$, $403_4$ or $403_6$ to change. Since the piezoelectric material is sensitive to environmental changes, e.g., temperature, a reference reflector $403_1$, $403_3$ or $403_5$ (e.g., an interdigital transducer) is used to provide a signal that enables the extraction of the active lithium concentration. Mechanical absorbers, e.g., 604, next to the input and output reflector $403_2$, $403_4$ or $403_6$ suppress reflections from other structures on the substrate or the edge of the substrate. In an example, the sensor load is matched to an optimal working point of reflector $403_4$. Since the GMI sensor 605 is an inductive element, matching is accomplished by a series capacitance resulting in load impedance given by the below equation $$Z=1/j\omega C_m+R+j\omega L(H_{ext}) \tag{1}$$

where $C_m$ is the matching capacitance, R is the average resistance (over the considered magnetic field range) of the GMI sensor, and $L(H_{ext})$ is the inductance of the GMI sensor.

Referring again to FIG. 7, the battery control module 703 is a control module in the electrified vehicle which receives information in analog format from SAW-GMI sensor system 702. In this example there are three communication channels 731, 732, 733 which connect BCM 8 to SAW-GMI sensor system 702. The CS_VREF signal on communication channel 731 provides a power supply and precision reference from the control module 703 to the SAW-GMI sensor system 702. In operation, the control module 703 provides a power source which allows circuits in the SAW-GMI sensor system 702 to operate. In an example, the CS_VREF signal is a combination of power supply and reference voltage to the SAW-GMI sensor system. The ground reference for the SAW-GMI sensor system is on communication channel 732 and is CS_REF signal. The third communication channel 733 includes an analog output signal to a digital output signal from the SAW-GMI system 702. In an example, the output signal on channel 733 is a voltage with range from 0 volts to CS_VREF volts. It is understood that the magnetic field from the lithiation in the battery or battery cell is being measured by the SAW-GMI sensor system 702, and the information about this field is coded by the circuitry in SAW-GMI sensor system 702 into an instantaneous voltage which appears as CS_AOUT on channel 733. In an example, a specific mathematical relationship between the instantaneous value of magnetic field passing through SAW-GMI element 714 and the instantaneous voltage of CS_AOUT on the third channel 733.

The SAW-GMI element 714 can include the reflector 403, the matching circuit, GMI sensor, and optionally a mechanical absorber that communicate with a transducer, which can communicate using the channels 731, 732, 733. In an example, a digital processor 715 receives an output from the SAW-GMI element 714 and processes the signal from the SAW-GMI element 714, e.g., using the mathematical relationship. The mathematical relationship can be in the form of instructions for processing the signal from the SAW-GMI element to an output to the digital to analog converter 722, which can also include a memory that acts as an input buffer or an output buffer. The digital processor 715 may also store a lookup table that allows an input to correlate to an output based on the mathematical relationship.

The control module 703 includes a buffer and filter circuitry 744 that is a terminal of the third channel 733. The buffer and filter circuitry 744 receives the output signal that represents the measured value of the battery lithiation. If the output signal from the SAW-GMI sensor system 702 is an analog signal an analog to digital converter 745 receives the signal from the buffer and filter circuitry 744. If the buffered and filtered signal that represents the voltage CS_AOUT signal on the third channel 733 is digital, then the buffer and filter circuitry can be connected directly to the master controller 750. Otherwise the A/D converter 745 outputs a digital signal to the controller 750. In an example, the A/D converter 745 is actually contained inside master controller 750. The master controller 750 can include processors, memory and other circuitry to receive inputs and produce output control signal(s) to the vehicle modules, including estimates of SOC, battery health and other battery state information, at least some of which are dependent or derived from the measurement from the SAW-GMI element 714.

The control module 703 may also include reference circuitry 755, which provides a combined power supply and precision reference signal to the SAW-GMI sensor 702, e.g., on the first communication channel 731 and the second communication channel 732. The reference circuitry can be connected to vehicle ground and to a supply rail, e.g., a B+ or 12V power supply feed from the vehicle, which is a standard automotive 12V power supply from the lead acid, non-traction battery of the electrified vehicle. The reference circuitry 755 may also pass the ground reference on the second communication channel 732 to the SAW-GMI sensor 702. In an example, the copper ground plane of the control module 703 is connected to the chassis reference in the vehicle. This copper ground plane of control module is available inside the reference circuitry, e.g., when circuitry is solid state. Another way of saying this is to say that communication channel 732 is at an equipotential with control module's ground plane, which is connected to vehicle chassis.

Figure 8:
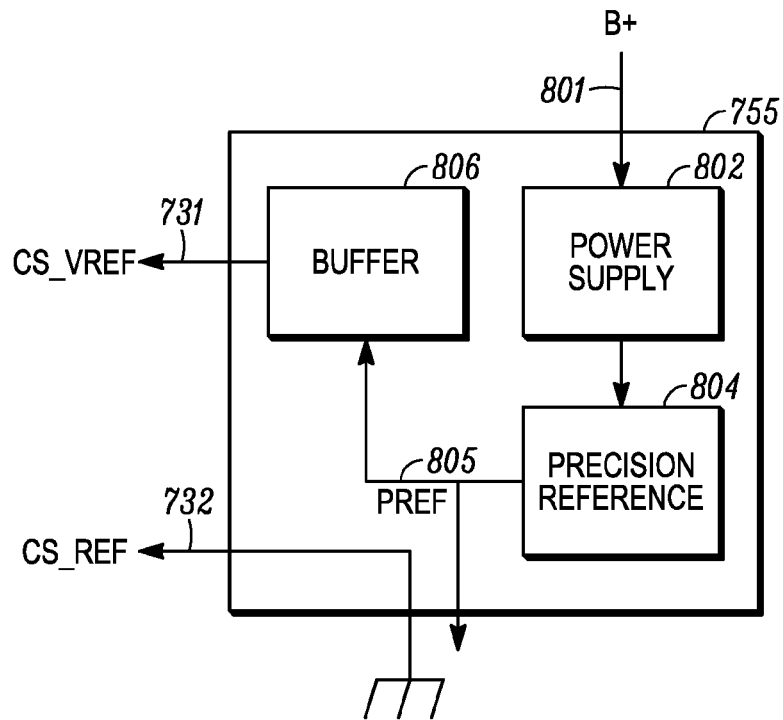
FIG. 8 is a schematic view of a reference circuit for a battery sensor system of an electric vehicle, according to an example embodiment

FIG. 8 shows the reference circuitry 755 to include to terminals connected to the communication channels 731, 732. The B+ power feed 801 into the reference circuitry 755, e.g., to the power supply circuitry 802. The power supply circuitry 802 converts the approximate 12V from the vehicle from B+ power feed 801 to a precision reference circuitry 804. The precision reference circuitry 804 outputs a precision regulated voltage (PREF) at terminal 805. The PREF signal is fed to a buffer circuit 806. In an example, the output from the buffer circuit 806 is to the first communication channel 731. The buffer circuit 806 is to ensure that the CS_VREF voltage is the same as PREF voltage. Buffer circuitry 806 should only allow a few millivolts drop from PREF 19, 20 to CS_VREF output to the communication channel 731. The result of the circuitry in reference circuitry block 755 is that the precision reference voltage CS_VREF output through the first channel 731 which is applied to the input of SAW-GMI sensor 702 is the same as the precision reference to A/D converter 745 in control module 703.

Referring back to FIG. 7, the SAW-GMI sensor 702 contains a SAW-GMI circuitry 714. This consists of a GMI thin film integrated with a SAW device and associated interfacing circuits. Interface circuits are able to translate the perturbations in the SAW-GMI into simple analog signal (a scalar voltage) that can be read by the digital processor 715. The placement of the SAW-GMI sensor 702 is such that the SAW-GMI element 714 is in close proximity to a lithium ion battery cell. As is further explained herein, the degree of lithiation in the cell is strongly related to the magnitude of the magnetic field which can be measured in the vicinity of the cell. GMI sensors are quite sensitive, for instance, with a range of ±300 μT and a sensitivity of 4 mV/μT. Since the integrated SAW-GMI sensor system 702 converts the magnetic field to a measurable voltage (CS_AOUT) on the third communication channel 733. In an example, the SAW-GMI sensor system 702 in such a way that when the magnetic field passing through SAW-GMI element 714 ranges from −300 μT to +300 μT, the voltage of output signal (CS_AOUT) ranges from +0.5V to +4.5V.

The output of the SAW-GMI element 714 may be an analog voltage which is fed into the digital processor circuitry 715 of SAW-GMI sensor system 702.

Figure 9:
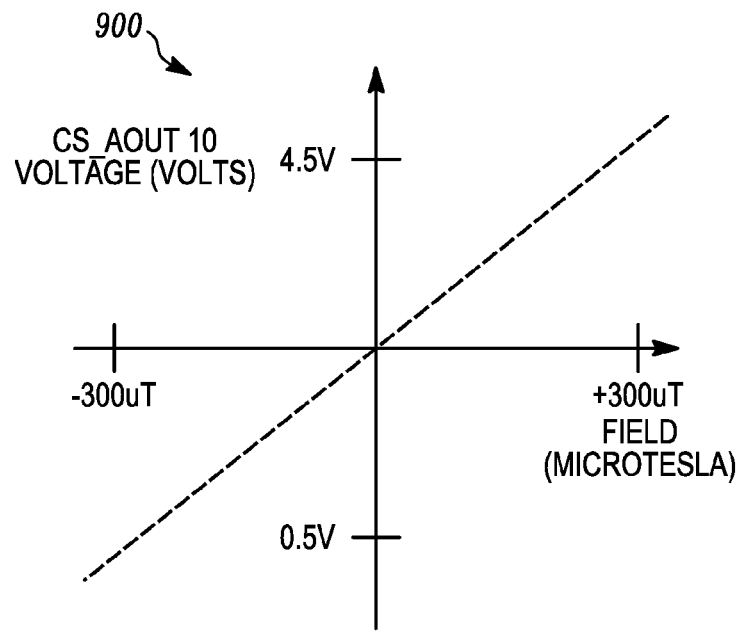
FIG. 9 shows a graph of field strength and output voltage for a battery sensor, according to an example embodiment.

FIG. 9 shows a graph 900 of a transfer function of magnetic field to the voltage output from the sensor subsystem 702, which measures lithium ions at a terminal in a battery cell. The sensor subsystem 702 measures the magnetic field and using the transfer function, which can be a formula or lookup table stored in the circuitry of the sensor subsystem 702, outputs a voltage signal of a digital signal representing a voltage to battery control module (BCM) 703. In an example, the magnetic field may range from about negative 300 microTeslas to 300 microTeslas. The output signal may range between 0.5 volts to 4.5 volts. The degree of lithiation in the battery cell is strongly related to the magnitude of the magnetic field which can be measured in the vicinity of the cell using the sensors described herein. In the GMI sensor example, the GMI sensor is sensitive, for instance, with a range of ±300 μT and a sensitivity of 4 mV/μT.

The present systems can be operated to wirelessly detect a state of a battery. A method may include wirelessly transmitting an input signal to the battery; receiving the input signal at a passive sensor connected to the battery; outputting a response signal that changes based on a modulus of the battery; and outputting battery state based on the response signal.

In an example, the input signal is a magnetic field.

In an example, the input signal is an electromagnetic signal and the sensor is a surface wave acoustic sensor that senses a magnetic field at an electrode of the battery. The SAW sensor includes a temperature sensor and a magnetic field sensor.

In an example, outputting the response signal includes wirelessly outputting the response signal from the surface wave acoustic sensor to a receiver outside the battery.

In use, Surface Acoustic Wave (SAW) based devices, which can be designed for wireless operation, provide a sensor platform for measuring active lithium concentration via magnetic field sensing. These sensors are based on the piezoelectric effect where by the propagation velocity of a SAW signal in a piezoelectric substrate changes in response to surface perturbation. SAW devices are sensitive to temperature, pressure, stress, liquid viscosity, and surface effects. In order to measure the magnetic field response for a charged/discharged cell, the surface of the SAW will have to be modified with a magnetic element to convert the magnetic field change into a surface perturbation. The present disclosure includes overlying the propagation path with a magnetoresistive (MR) film, giant magnetoimpedance (GMI) thin film or embedding a permanent magnet in a cantilever substrate structure. Among the available magnetic field sensors, SAW-based thin film GMI offers favorable characteristics such as high frequency sensitivity to magnetic field, compatibility with high frequency operation and standard microfabrication procedures, and easy integration with SAW devices and electronic circuits.

The systems and methods described herein can measure temperature at and within each battery cell and state of charge. Specifically, using smart sensor systems that can be embedded with the battery cell direct measurement of the physical characteristics or internal state of the battery cell can provide more precise knowledge of the operating state of the battery cell. This knowledge can be used in control techniques for the battery cell and vehicle. The use of passive sensors with wireless communication allows the direct measurement of battery cell characteristics, which heretofore was not possible. As these direct measurements were not done, control algorithms made assumptions that may not be accurate or may operate in an inefficient manner. These direct measurements can be used on their own or in combination with cell voltage measurement techniques.

The sensors and tags described herein are packaged to withstand the vehicle environment. The vehicle environment includes the temperature and moisture as well as the vibrations associated with vehicle travel and engine vibrations. The sensors and tags if mounted to or within the battery are further packaged to withstand the temperature range −40° C. to 75° C. (storage: 85° C.) and possible caustic environment of batteries. The sensors can communicate wirelessly with other communication devices within the vehicle or with paired components. The sensor systems described herein can observe the internal states of the battery and use this information to determine information, e.g., voltage, SOC, localized temperature, state of health, etc. These sensor systems are believed to be low maintenance compared to current sensors as they do not have batteries or other power sources to be replaced or replenished or connected. These sensors have a small size, on the order of a grain of rice in some instance, and hence ensure unobtrusive deployment either on the battery or in the battery. It is believed that these sensors may facilitate the deployment of multiple sensors to form a distributed wireless sensor network as well as maintain electromagnetic compliance with the vehicle as these devices are low power with small electromagnetic fields.

The present disclosure uses the term chips, which can be circuitry, integrated circuits, packaged circuits, micro-electro-mechanical systems (MEMS) or combinations thereof that can perform the functions described herein. The chips, in various examples, may have to meet the environmental extremes of internal battery conditions, battery packaging, or mounting in a vehicle that is subject to high heat and freezing conditions and remain operable.

The present disclosure, in various embodiments, addresses the needs of electrified vehicles with a high voltage battery being used as traction battery. The controls for electrified vehicles have two parameters which must be estimated, i.e., the state of charge (SOC) and capacity of each cell. Prior methods do not measure SOC and capacity directly, but are estimated based on the inputs of voltage, current, and temperature. A large number of techniques exist as to how to estimate SOC and capacity. It should be noted that there is not a simple relationship between cell voltage, current, temperature, and SOC, the voltage of a cell is a path function, especially with respect to the history of current over the recent past. To add to the complexity, the cell voltage, what can be measured, is actually the difference of two voltages, that of the reactions at each of the two electrodes in the cell. Even open circuit voltage (OCV) at rest, the prior best measure of voltage, for state of charge correlations for those battery chemistries where there is a good relationship between OCV and SOC is not perfect, not only must the battery be at rest for an amount of time, but the SOC/OCV relationship itself changes over time under certain circumstances.

Knowledge of the capacity of a battery is important for applications such as a battery electric vehicle where remaining range (distance to empty) must be estimated. Although the capacity of a new battery is known, it changes over time, often significantly. Prior methods call for capacity to be calculated as the ratio of the charge used to the difference in states of charge over the range, as shown in the equation below. This is subject to significant errors, that of the current integration and that of the beginning and ending states of charge, so care must be taken as to when capacity is calculated. An example of estimating can be found in U.S. Pat. No. 8,751,086.

$$Q = \frac{\int I dt}{SOC_f - SOC_i} \quad (2)$$

The presently described methods and systems provide direct measurement of the state of charge and/or capacity of a lithium cell of the type used in electrified vehicles. This may provide a non-invasive method that directly measures concentration of active lithium in positive electrode. The present disclosure may be free of cumulative errors will be present in the prior art SOC calculation, e.g., as compared to coulomb counting. In use, the present methods and systems may be used as an inexpensive laboratory tool to monitor the cell behavior as will be seen in actual usage, i.e., a "reference electrode" that does not participate in cell reactions. The sensor device can be designed to measure both temperature and concentration of active lithium. Since device can be configured to communicate in a wireless manner, this will eliminate NTC thermistor and the associated wires used in the battery pack today to measure temperature. It will be recognized that the SOC is not determined merely by the integration of the current.

While exemplary embodiments are described above, it is not intended that these embodiments describe all possible forms of the invention. Rather, the words used in the specification are words of description rather than limitation, and it is understood that various changes may be made without departing from the spirit and scope of the invention. Additionally, the features of various implementing embodiments may be combined to form further embodiments of the invention.

What is claimed is:

1. A vehicle comprising:
an electric motor;
a battery to store electrical energy for the electric motor; and
a surface acoustic wave sensor to wirelessly sense a magnetic field of the battery and temperature of the battery, the sensor including a magnetic field reactive device to change a surface wave in response to the magnetic field as a function of lithiation at an electrode of the battery.

2. The vehicle of claim 1, wherein the surface acoustic wave sensor includes a passive radio frequency identification tag.

3. The vehicle according to claim 1, further comprising control circuitry to control the electric motor and the battery based on an output signal from the surface acoustic wave sensor.

4. The vehicle of claim 3, wherein the control circuitry sets a battery state from the output signal from the surface acoustic wave sensor.

5. The vehicle of claim 4, further comprising circuitry to derive state of charge (SOC) or state of health (SOH) from the magnetic field as sensed by the surface acoustic wave sensor.

6. The vehicle of claim 1, wherein the surface acoustic wave sensor is embedded in a housing of the battery and wirelessly communicates with control circuitry of the electric motor.

7. The vehicle of claim 1, wherein the surface acoustic wave sensor includes a plurality of acoustic reflectors, and converts an input signal to a surface wave acoustic signal that is reflected by the reflectors to produce a response signal and modified by the magnetic field reactive device.

8. The vehicle of claim 7, wherein the magnetic field reactive device includes a giant magnetoimpedance (GMI) thin film.

9. The vehicle of claim 8, further comprising a mechanical absorber on the surface acoustic wave (SAW) substrate adjacent to the GMI thin film and matching circuitry electrically connecting the GMI thin film to at least one of the plurality of acoustic reflectors.

10. The vehicle of claim 9, wherein the at least one of the plurality of acoustic reflectors includes an interdigated reflector with a finger having at thickness of $\lambda/8$ relative to a signal on the SAW substrate.

11. The vehicle of claim 8, wherein the surface acoustic wave sensor includes circuitry to convert sensed magnetic field to an output voltage.

12. A battery monitoring system comprising:
a surface acoustic wave sensor to wirelessly sense a state of a battery and having a magnetic field sensing device to modify a SAW signal based on a magnetic field at a battery electrode, a temperature sensor to sense temperature at a battery, and a transducer to wirelessly output an output signal including temperature and battery state; and
control circuitry to convert the sensed magnetic field to an output voltage signal.

13. The battery monitoring system of claim 12, wherein the surface acoustic wave sensor includes a passive radio frequency identification tag.

14. The battery monitoring system of claim 12, wherein the control circuitry converts the output voltage signal to a state of charge (SOC) or a state of health (SOH).

15. The battery monitoring system of claim 12, wherein the surface acoustic wave sensor is embedded in a housing of the battery.

16. A battery monitoring system comprising:
a surface acoustic wave sensor to wirelessly sense a state of a battery and having a magnetic field sensing device to modify a SAW signal based on a magnetic field at a battery electrode, a temperature sensor to sense temperature at a battery, and a transducer to wirelessly output an output signal including temperature and battery state; and
control circuitry to convert the sensed magnetic field to an output voltage signal,
wherein the surface acoustic wave sensor includes a plurality of acoustic reflectors, and the magnetic field sensing device includes a giant magnetoimpedance (GMI) thin film connected to at least one of the acoustic reflectors.

17. The battery monitoring system of claim 16, wherein the magnetic field sensing device includes a mechanical absorber adjacent one of the acoustic reflector and the GMI thin film.

18. The battery monitoring system of claim 17, wherein the magnetic field sensing device includes matching circuit connected to the acoustic reflector and the GMI thin film.

19. The battery monitoring system of claim 18, wherein the transducer includes conversion circuitry to convert the sensed magnetic field to an output signal to be wirelessly transmitted from the surface acoustic wave sensor to external circuitry at a vehicle.

20. The battery monitoring system of claim 19, wherein the at least one of the acoustic reflectors includes an interdigitated reflector with a finger having at thickness of $\lambda/8$ relative to a signal on a substrate of the surface acoustic wave sensor.

* * * * *